(12) United States Patent
Testoni (10) Patent No.: US 7,132,652 B1
(45) Date of Patent: Nov. 7, 2006

(54) AUTOMATIC CLASSIFICATION OF DEFECTS USING PATTERN RECOGNITION APPLIED TO X-RAY SPECTRA

(75) Inventor: Anne L. Testoni, Bolton, MA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 102 days.

(21) Appl. No.: 10/811,319

(22) Filed: Mar. 25, 2004

Related U.S. Application Data (60) Provisional application No. 60/457,958, filed on Mar. 25, 2003.

(51) Int. Cl.
*G01N 23/00* (2006.01)
*G21K 7/00* (2006.01)

(52) U.S. Cl. .................. 250/310; 250/310; 250/307
(58) Field of Classification Search ............. 250/307, 250/310
See application file for complete search history.

(56) References Cited

U.S. PATENT DOCUMENTS

| 5,877,498 | A | | 3/1999 | Sugimoto et al. | 250/310 |
| 5,893,095 | A | | 4/1999 | Jain et al. | 707/6 |
| 5,911,139 | A | | 6/1999 | Jain et al. | 707/3 |
| 6,072,178 | A | * | 6/2000 | Mizuno | 250/310 |
| 6,104,835 | A | | 8/2000 | Han | 382/225 |
| 6,233,719 | B1 | | 5/2001 | Hardikar et al. | 716/1 |
| 6,407,386 | B1 | * | 6/2002 | Dotan et al. | 250/310 |
| 6,583,413 | B1 | * | 6/2003 | Shinada et al. | 250/310 |
| 6,787,773 | B1 | | 9/2004 | Lee | 250/311 |
| 6,855,930 | B1 | * | 2/2005 | Okuda et al. | 250/310 |

FOREIGN PATENT DOCUMENTS

WO WO/01/40145 A2 6/2001

* cited by examiner

*Primary Examiner*—Jack Berman
*Assistant Examiner*—Jennifer Yantorno
(74) *Attorney, Agent, or Firm*—Beyer Weaver & Thomas, LLP (57) ABSTRACT

Disclosed are methods and apparatus for classifying defects based on X-ray spectrum obtained from the defects. In general terms, the present invention provides pattern recognition techniques for accurately and efficiently classifying a defect based on an X-ray spectrum obtained from such defect and its surrounding substrate and structures, no matter the complexity of such substrate and structures. A pattern recognition technique generally includes training a pattern recognition process to recognize particular types of X-ray spectrum obtained from specimens as belonging to a particular defect type or other specific characteristic of a specimen. Once a pattern recognition process is set up to recognize or classify particular X-ray spectrum, the pattern recognition process can then be utilized to automatically classify specimens as having a specific characteristic or defect type.

27 Claims, 9 Drawing Sheets

AUTOMATIC CLASSIFICATION OF DEFECTS USING PATTERN RECOGNITION APPLIED TO X-RAY SPECTRA

CROSS REFERENCE TO RELATED PATENT APPLICATION

This application claims priority of U.S. Provisional Application No. 60/457,958 filed on Mar. 25, 2003, entitled AUTOMATIC CLASSIFICATION OF DEFECTS USING PATTERN RECOGNITION APPLIED TO X-RAY SPECTRA, by Anne Testoni which is incorporated herein by reference in its entirety for all purposes.

BACKGROUND OF THE INVENTION

The present invention relates generally to inspection of semiconductor devices for the purpose of identifying defects thereon. Additionally, it relates to techniques for classifying defects found on integrated circuit devices.

Semiconductor defects may include structural flaws, residual process material and other surface contamination which occur during the production of semiconductor wafers. Defects are typically detected by a class of instruments called inspection tools. Such instruments automatically scan wafer surfaces and detect, and record the location of optical anomalies using a variety of techniques. This information, or "defect map," is stored in a computer file and sent to a defect review station.

Using the defect map to locate each defect, a human operator observes each defect under a microscope and classifies each defect according to class (e.g., particle, pit, scratch, or contaminant). Information gained from this process is used to correct the source of defects, and thereby improve the efficiency and yield of the semiconductor production process. Problems with this classification method include the technician's subjectivity in identifying the defect class, and the fatigue associated with the highly repetitive task of observing and classifying these defects.

One type of inspection or review tools that may be used to classify a defect are electron beam (ebeam) induced X-ray tools. An ebeam induced X-ray tool directs an e-beam towards the defect and X-rays are emitted from the defect as well as any surrounding material in response to the e-beam. The X-rays may then be analyzed to determine a composition of the defect. Typically, the X-rays are compared to X-rays emitted from a substrate having no defect. The X-ray spectra for the substrate without a defect is subtracted from the substrate having the defect to obtain the X-ray spectra for the defect. Although one can easily determine a composition of a defect when the substrate is formed from a single material, such as silicon, it becomes rather difficult to identify a defect's composition when the substrate is complex and formed from several different structures and materials. This technique would require obtaining reference X-ray spectra from multiple substrate specimens having no defects to thereafter compare to defects on such complex substrates. Additionally, one would have to determine the substrate type for each type of defect and then use the appropriate reference X-ray spectra to determine the defect's composition.

Accordingly, there is a need for improved mechanisms for classifying defects using an e-beam induced X-ray inspection or review system or the like.

SUMMARY OF THE INVENTION

Accordingly, mechanisms are provided for classifying defects based on X-ray spectrum obtained from the defects. In general terms, the present invention provides pattern recognition techniques for accurately and efficiently classifying a defect based on an X-ray spectrum obtained from such defect and its surrounding substrate and structures, no matter the complexity of such substrate and structures. A pattern recognition technique generally includes training a pattern recognition process to recognize particular types of X-ray spectrum obtained from specimens as belonging to a particular defect type or other specific characteristic of a specimen. Once a pattern recognition process is set up to recognize or classify particular X-ray spectrum, the pattern recognition process can then be utilized to automatically classify specimens as having a specific characteristic or defect type.

In one embodiment, a method of classifying specimens based on X-ray data obtained from such specimens is disclosed. X-ray data is provided from a plurality of known specimens having known characteristics which are classified into a plurality of known classes. A pattern recognition process is set up to automatically classify the known characteristics of the known specimens based on the X-ray data from the known specimens. X-ray data can then be provided from an unknown specimen having an unknown characteristic of an unknown class. The pattern recognition process is utilized to automatically classify the unknown characteristic of the unknown specimen based on the X-ray data from the unknown specimen.

In a specific implementation, the X-ray data from the known specimens is provided by directing a charged particle beam toward each known specimen and detecting X-rays emitted from the each known specimen in response to the charged particle beam. The detected X-rays form X-ray data have one or more intensity values at one or more energy levels. The X-ray data from the unknown specimen are provided in a similar manner.

In one aspect, the unknown specimens and the known specimen are each a semiconductor device or test structure. In another aspect, the known and the unknown characteristic are each a defect and the known classes are known defect classes. In one embodiment, the known defect classes include defect compositions. In a further aspect, each known defect class includes one or more characteristics selected from the following: a particular defect composition, a defect location, an electrical type defect, an open type defect, etc.

In a specific embodiment, setting up the pattern recognition process is accomplished by training a pattern recognition process to recognize particular types of X-ray data as belonging to one of the known classes. In a more specific embodiment, the pattern recognition process is a neural net algorithm, a natural grouping algorithm, or a wavelet algorithm. In yet another specific aspect, setting up the pattern recognition process is accomplished by (a) associating a feature vector having a plurality of parameters with each known specimen based on the each know specimen's X-ray data; (b) selecting a set of weight values for each variable in a class code equation; (c) inputting the selected weight values and the parameters of each feature vector into the class code equation to determine a plurality of class codes for the known specimens; (d) adjusting the weight values until the class codes for the known specimens having a same known class result in a same class code value; and (e) storing the weight values and class code values for the known specimens.

In a further implementation, utilizing the pattern recognition process to automatically classify the unknown characteristic of the unknown specimen based on the X-ray data from the unknown specimen is accomplished by (a) associating a feature vector having a plurality of parameters with the unknown specimen; (b) inputting the stored weight values and the parameters of the feature vector of the unknown specimen into the class code equation to determine a class codes for the unknown specimen; (c) comparing the class code for the unknown specimen to the stored class codes for the known specimens; and (d) when the class code for the unknown specimen matches a one of the stored class codes, classifying the unknown specimen based on the matching class code. In a specific embodiment, the parameters of each feature vector of the known specimens and the unknown specimen include intensity values for each X-ray peak and its associated energy level and/or one or more ratios of X-ray intensity values.

In another aspect, the invention pertains to an apparatus for classifying specimens based on X-ray data obtained from such specimens. The apparatus includes a beam generator operable to direct a charged particle beam towards a specimen, a detector positioned to detect X-rays from the specimen in response to the charged particle beam, and a processor operable to perform one or more of the above described method operations.

These and other features of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Generally, the present invention applies to inspecting defects in or on wafers using X-ray emission techniques. X-ray emission analyses involves characterizing the composition of a specimen by exciting the atomic core electrons within a specimen and analyzing the resulting emitted X-rays. In the present invention, excitement of the atomic core electrons is achieved by bombarding the specimen with a focused electron beam (e-beam), although other techniques of inducing X-ray emission such as a focused ion beam can be used. Upon specimen bombardment, a transfer of energy occurs which excite the atomic core electrons into different electronic energy levels. Once in this excited state, the atoms have two possible modes of relaxation: emission of X-rays, or emission of Auger electrons.

Figure 1:
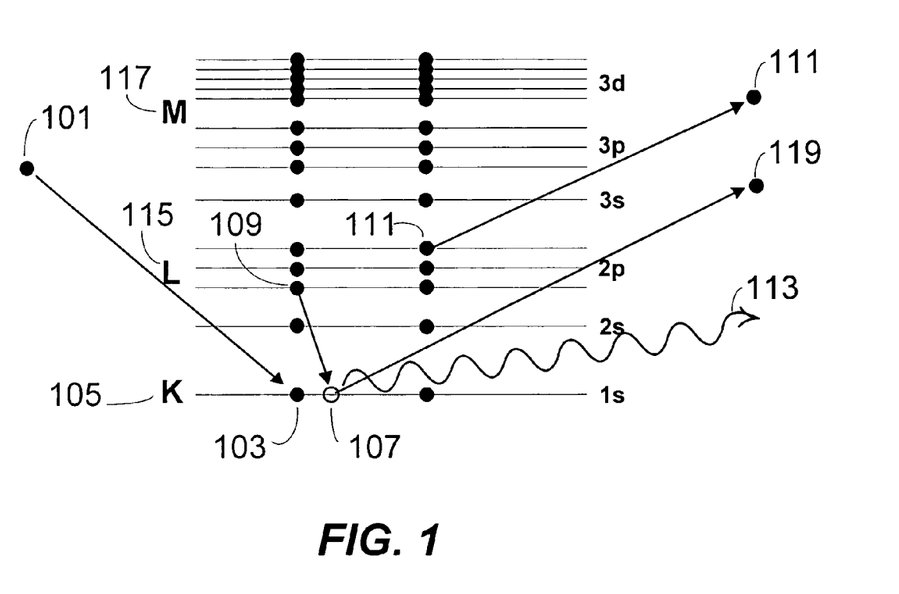
FIG. 1 is a diagram of a Bohr model of an atom showing electronic transitions during Auger electron emission and X-ray emission competing processes.

To illustrate these two possibilities, FIG. 1 illustrates a Bohr model of an atom with three electronic energy levels K, L and M (105, 115 and 117, respectively), with electrons in K having greater electronic binding energy than those in L, and electrons in L having greater binding energy than those in M. An incident electron 101 strikes an atom with enough energy to displace an atomic core electron 103, causing the ejection of a secondary electron 119 and producing a core hole or vacancy 107. With the vacancy in the core energy level, the atom is energetically unstable. The most probable stabilization mechanism is filling the vacancy with another electron in a higher energy level 109. That is, a second electron falls from a higher level into the vacancy with release of energy. The resulting energy may then be carried off by one of two mechanisms: Auger electron emission or X-ray emission. In Auger electron emission, the resulting energy is carried off when an Auger electron 111 from a higher energy level is ejected. In X-ray emission, the resulting energy is carried off in the form of emitted X-rays 113, leaving an ionized atom. Auger electron emission and X-ray emission are competitive processes.

The present invention pertains to the detection and analysis of X-ray emissions of a specimen in accordance with the above description. Each element has its own characteristic electronic energy configurations and its own characteristic X-ray emissions. For example, copper has two dominant characteristic X-ray emissions: an L$\alpha$ emission (emitted when an electron falls into the L electronic energy level) with an associated energy of about 0.93 kilo electron volts (keV); and a K$\alpha$ emission (emitted when an electron falls into the K electronic energy level) with an associated energy of about 8.04 keV. Other elements will have their own characteristic associated energy transitions and X-ray emissions.

Figure 2:
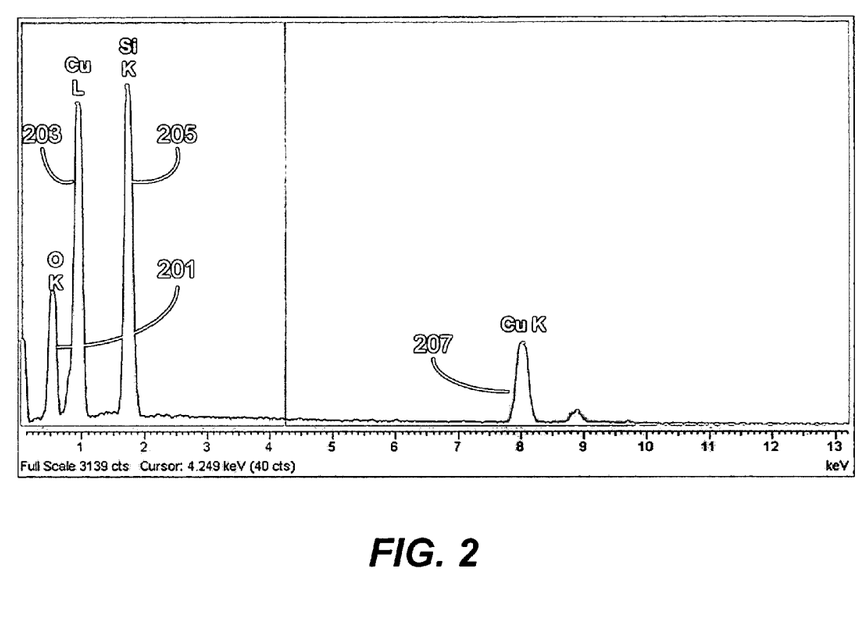
FIG. 2 is an X-ray emission spectrum from a copper semiconductor integrated device specimen.

The X-ray emissions of a specimen can be collected in the form of an X-ray emission energy spectrum. For example, FIG. 2 is an X-ray emission energy spectrum from a copper interconnect structure in an integrated circuit. The horizontal axis represents energy in keV and the vertical axis is the relative intensity. The oxygen Kα (O Kα) peak 201 has an energy of about 0.93 keV. The copper Lα (Cu Lα) peak 203 has a larger intensity than the O Kα and has an energy of around 1 keV. The silicon Kα (Si Kα) peak 205 has a larger intensity than the Cu Lα and O Kα peaks and has an energy of almost 2 keV. The copper Kα peak (Cu Kα) 207 has a lower intensity than the O Kα, Cu Lα and Si Kα peaks and has an energy of about 8.04 keV. The relative intensities of the peaks in this X-ray spectrum can be compared to spectra of the pure elements or other specimens of known composition to determine the elemental composition and amounts of each element within the specimen.

Figure 3A:
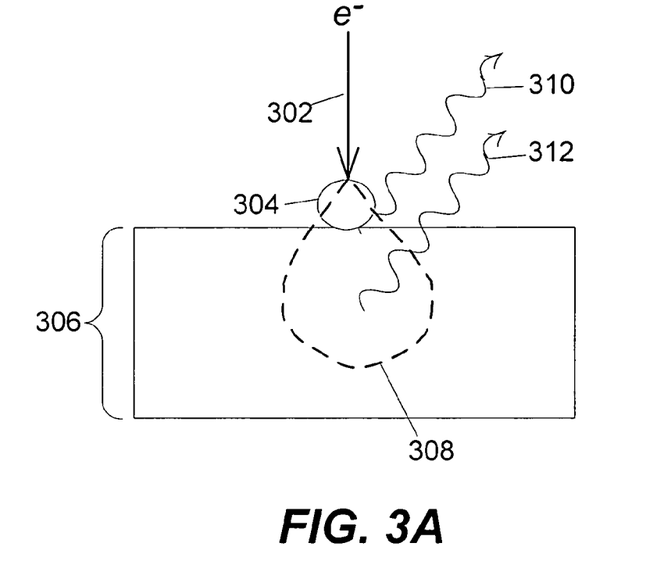
FIG. 3A illustrates a cross section of a semiconductor specimen having a defect with an electron beam incident upon the specimen, resulting in X-rays being emitted by the defect and underlying substrate.

In a preferred embodiment of the invention, X-ray emission is induced with an electron beam (e-beam). If the e-beam is of sufficient energy, bombardment of a specimen will result in an approximately "teardrop" shaped region, or volume, of excitation within the specimen. This teardrop volume is depicted in FIG. 3A. The figure illustrates a cross sectional view of a defect 304 on top of a silicon substrate 309 being bombarded by a focused e-beam 302. The defect in this example is composed of silicon dioxide. The e-beam bombardment results in a teardrop shaped volume 308 wherein electron trajectories travel, thereby causing X-ray emission from the defect and the silicon substrate, in the form of X-rays 310 and 312, respectively. This teardrop region is three-dimensional in that it covers a teardrop shaped volume within the specimen. An X-ray detector (not shown) is positioned to detect emitted X-rays from this teardrop region.

Note that the incident e-beam will preferably have a high enough energy to generate X-rays from the defect and a portion of the substrate. This e-beam energy will depend on the specimen composition and thickness and on how deeply the defect to be examined lies or how deeply a defect can possibly lie.

Figure 3B:
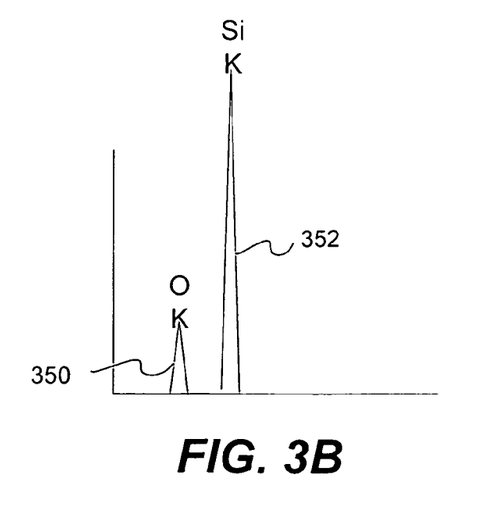
FIG. 3B is an X-ray emission energy spectrum obtained from the defect and underlying substrate of FIG. 3A.
Figure 3C:
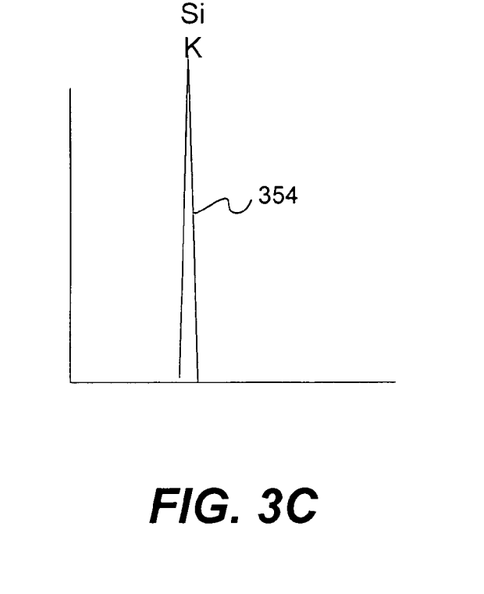
FIG. 3C is an X-ray emission energy spectrum from a reference silicon substrate having no defects.

FIG. 3B is an X-ray emission energy spectrum obtained from the defect 306 and underlying substrate 306 of FIG. 3A. The horizontal axis represents energy in keV and the vertical axis is the relative intensity. As shown, the spectrum includes an oxygen Kα (O Kα) peak 350 and a silicon Kα (Si Kα) peak 352 that has a larger intensity than the O Kα peak. FIG. 3C is an X-ray emission energy spectrum from a reference silicon substrate having no defects. This spectrum only includes only a silicon Kα (Si Kα) peak 354 which has an energy of almost 2 keV.

Figure 3D:
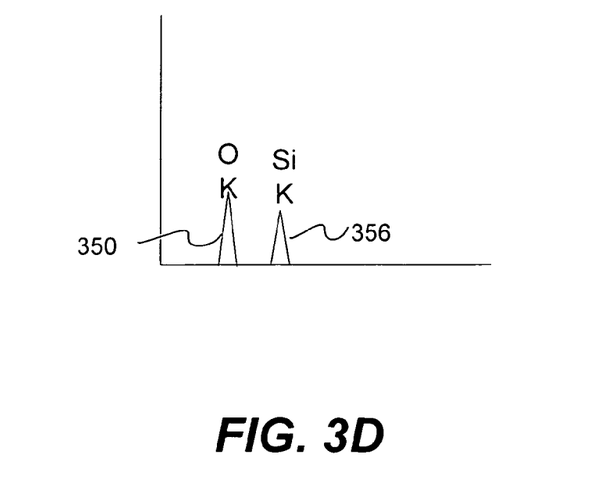
FIG. 3D is an X-ray emission energy spectrum which results from subtracting the spectrum obtained from the reference silicon substrate having no defects from spectrum obtained the substrate having a defect.

In conventional techniques, the relative intensities of the peaks in the X-ray spectrum obtained from the substrate having the defect can be compared to the spectrum obtained from the reference substrate having no defects to determine the composition of the defect. For example, subtracting the spectrum obtained from the substrate without a defect (of FIG. 3C) from the spectrum obtained from the substrate having a defect (of FIG. 3B) results in the spectrum of FIG. 3D. The resulting spectrum of FIG. 3D has a lower Si Kα peak intensity 356 than the Si Kα peak in the FIG. 3B spectrum and a same O Kα peak prior to the subtraction. One may determine that the defect of FIG. 3A is composed of silicon dioxide based on the presence of the Si and O peak within the resulting spectrum of FIG. 3D.

Figure 4A:
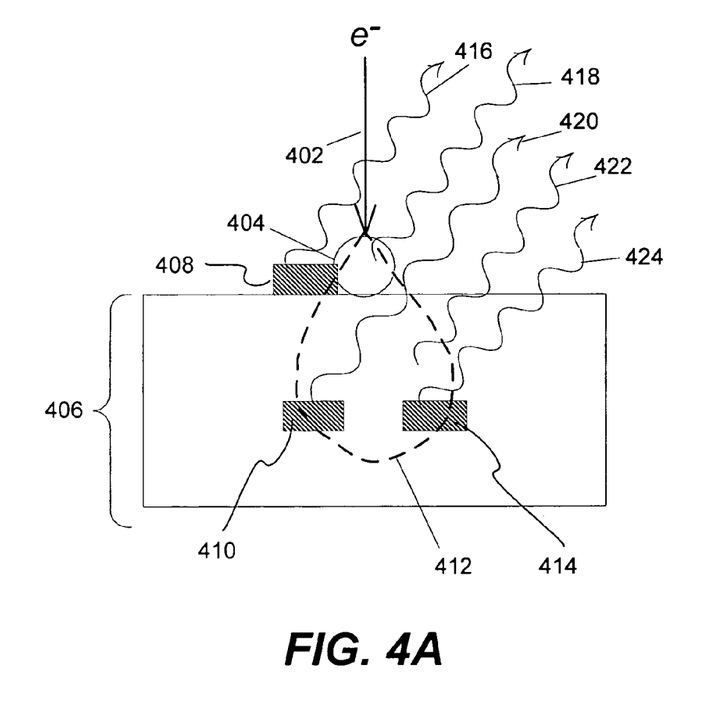
FIG. 4A illustrates a cross sectional view of a complex substrate 406 having a plurality of conductive copper structures.
Figure 4B:
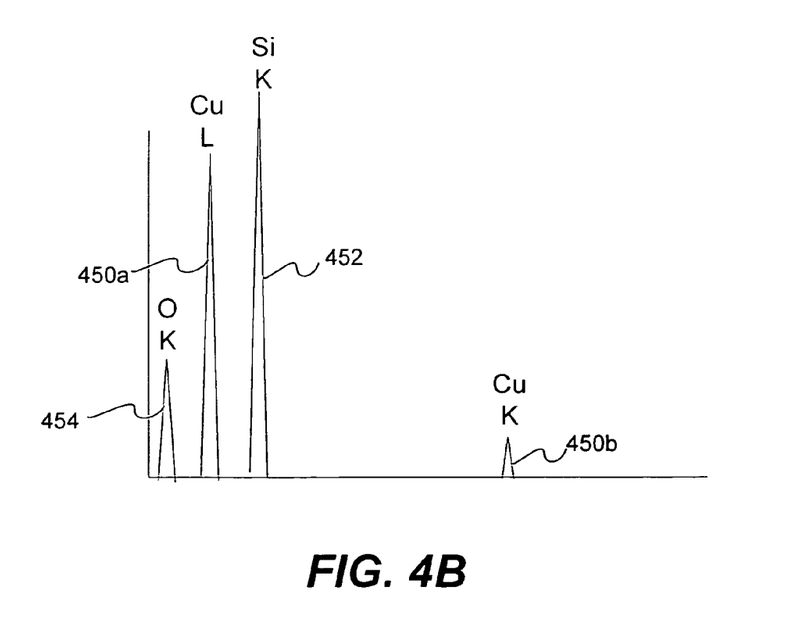
FIG. 4B is an X-ray emission energy spectrum obtained from the defect and underlying complex substrate of FIG. 4A.

However, this technique does not work when the substrate is more complex. By way of example, FIG. 4A illustrates a cross sectional view of a complex substrate 406 having a plurality of conductive copper structures 408, 410, and 414. In this example, X-rays are emitted from the copper structures 408, 410, and 414, as well as the silicon substrate 406 and defect 404, shown as X-rays 416, 420, 424, 422, and 418, respectively. As shown in FIG. 4B the spectrum for the complex substrate of FIG. 4A includes an oxygen Kα peak 454, a copper Lα peak 450a, a copper Kα peak 450b, and a silicon K peak 452. Subtracting the reference spectrum, for example, of FIG. 3C from the spectrum obtained from such a complex substrate does not facilitate determination of the defect's composition. Generating spectrum from a suitable number of reference substrates for comparison to the diverse number of complex substrates which could contain a defect would be a nearly impossible task.

In general terms, the present invention provides pattern recognition techniques for accurately and efficiently classifying a defect based on an X-ray spectrum obtained from such defect and its surrounding substrate and structures, no matter the complexity of such substrate and structures. Accordingly, classification techniques of the present invention provide an efficient and accurate mechanism for automatically classifying unknown specimens. These techniques allow classification of defects on a wide range of complex substrates.

Figure 5:
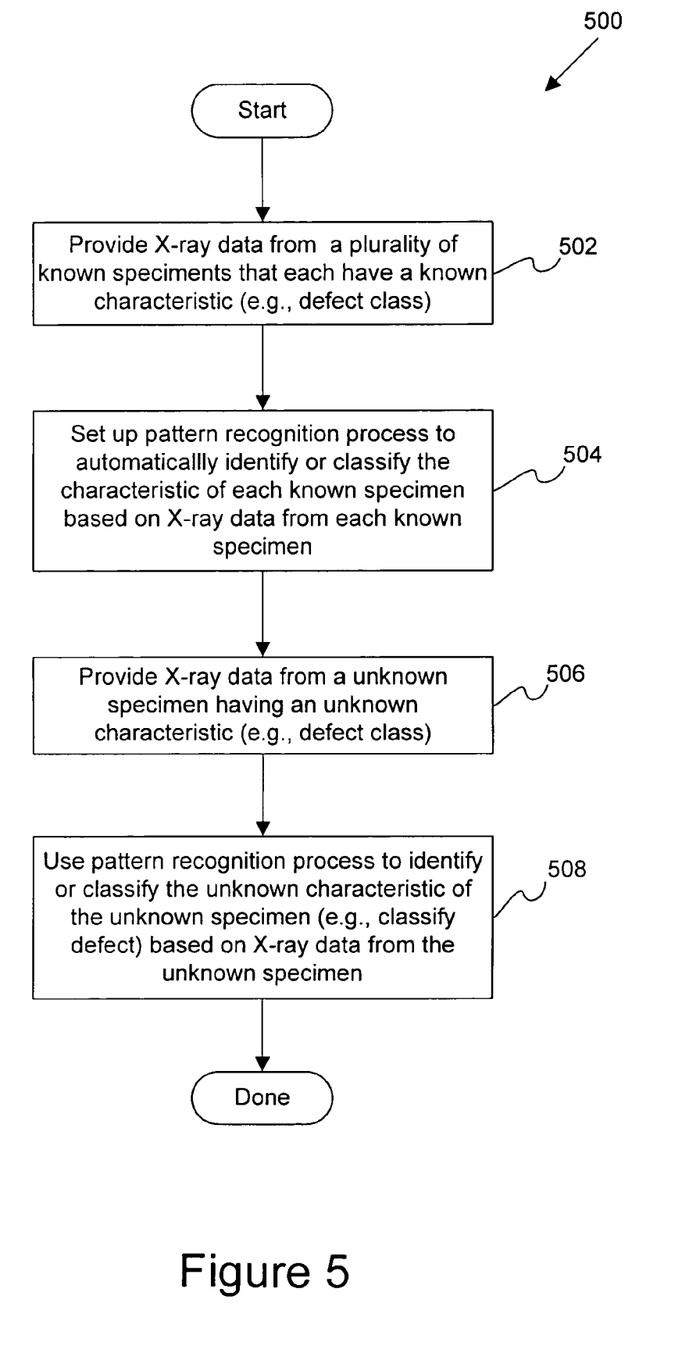
FIG. 5 is a flowchart illustrating a procedure for classifying defects and other characteristics of the specimen based on X-ray data in accordance with one embodiment of the present invention.

FIG. 5 is a flowchart illustrating a procedure 500 for classifying defects and other characteristics of the specimen based on X-ray data in accordance with one embodiment of the present invention. Initially, X-ray data is provided from a plurality of known specimens that each have known characteristics or classes, such as known defect types, in operation 502. In one implementation, a charged particle beam (e.g., an electron beam) is directed toward each known specimen, and X-rays emitted from the each known specimen in response to the charged particle beam are detected. The detected X-rays are in the form X-ray data having one or more intensity values at one or more energy levels.

Typically, the specimen is in the form of a semiconductor device or test structure. However, any suitable type of specimen which may be characterized using X-ray data may be used in the present invention. By way of examples, a thin film on a computer disk may be characterized by X-rays. The known characteristic of each known specimen may include any suitable parameter that may be characterized by X-rays. In one embodiment, the known characteristic is a defect class and corresponds to a particular defect composition, a defect location relative to the substrate, a via, or a trench, an electrical short type defect, an electrical open type defect, etc. The known characteristic or class may also correspond to other characteristics of the specimen, besides a defect class, such as film thickness. In this embodiment, X-ray data is provided from a plurality of specimens having known defect classes or compositions.

A pattern recognition process is then set up to automatically identify or classify the characteristic of each known specimen based on the X-ray data from each known specimen in operation 504. Any suitable pattern recognition technique may be used to classify or identify characteristics of a specimen based on X-rays data. In general terms, a pattern recognition technique includes training a pattern recognition process to recognize particular types of X-ray spectrum as belonging to a particular defect type or other specific characteristic of a specimen. Example pattern recognition algorithms that may be modified for recognizing different X-ray spectrum as belonging to a particular class of defects include neural net, natural grouping, and wavelet algorithms.

Several example pattern recognition techniques for classifying images are described further in U.S. Pat. No. 6,104,835, issued 15 Aug. 2000, by Ke Han (herein referred to as the '835 patent), which patent is herein incorporated by reference in its entirety for all purposes. These pattern recognition techniques may easily be modified and applied to X-ray spectrum, instead of images. For instance, the pattern recognition techniques described in the '835 patent utilize descriptor vectors that include image parameters that characterize the images. These descriptors may be modified to include X-ray data parameters, as well as other information relevant for characterizing a defect or other characteristic of a specimen.

After a pattern recognition process is set up, X-ray data may then be provided from a unknown specimen having a unknown characteristic in operation 506. For example, the specimen may have a defect that has not been classified yet. The X-ray data from an unknown specimen may be provided in the same manner as described above with respect to providing X-ray data from a known specimen. The pattern recognition process is then used to identify or classify the unknown characteristic of the unknown specimen based on the X-ray data from unknown specimens in operation 508. Operations 506 and 508 may be repeated to classify any number and type of specimens.

Figure 6:
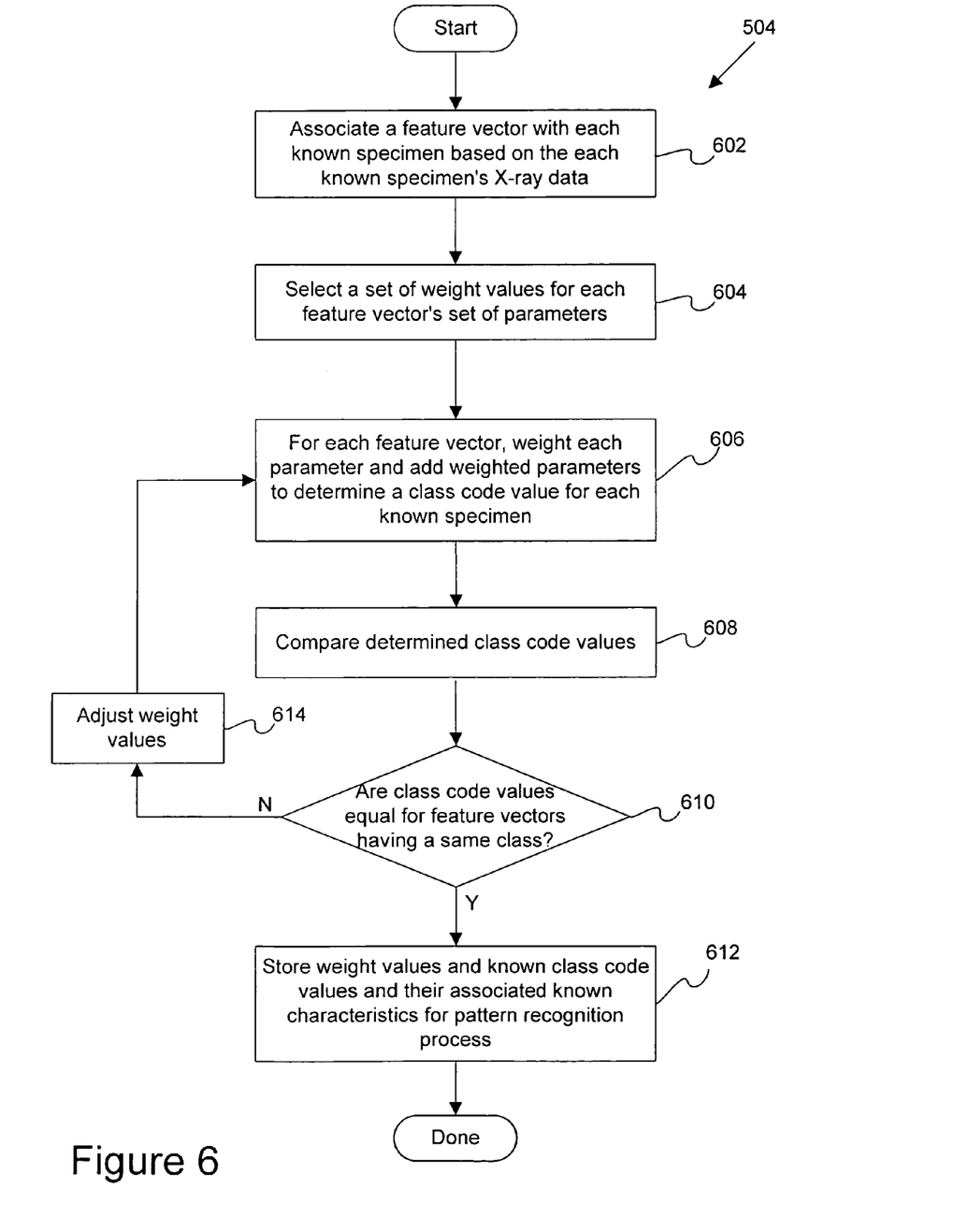
FIG. 6 is a flowchart illustrating the operation of FIG. 5 for setting up the pattern recognition process in accordance with one embodiment of present invention.

FIG. 6 is a flowchart illustrating the operation 504 of FIG. 5 for setting up the pattern recognition process in accordance with one embodiment of present invention. Initially, a feature vector is associated with each known specimen based on the each known specimens X-ray data in operation 602. The parameters of each feature vectors may include any information associated with the specimen, as well as any suitable X-ray data. By way of examples, the feature vector may include values for each X-ray peak intensity and its associated energy level, ratios of particular X-ray peak intensities (e.g., Si/O), defect size, etc.

A set of weight values are then selected for each variable in a class code equation in operation 604. One example of a class code equation for a three parameter feature vector is:

$$C=aA+bB+cC+dD+eAB+gAC+hBC+iA^2+jB^2+kC^2 \quad [1]$$

where a~k are weight values, and A~C are feature vector parameters. Of course, the class code and weight values will vary with different sized feature vectors. Additionally, different variables may be used depending on the particular requirements of the defect or specimen characteristic analysis application. The selected weights and the parameters of each feature vector are input into the class code equation in operation 606.

After class code values are determined for the feature vectors from the known specimens, the determined class code values are then compared to each other in operation 608. It is then determined whether the class code values are equal for the feature vectors having a same class in operation 610. Using the above equation 1 in an example, a first defect class results in C equaling "1" for feature vectors obtained from specimens having the first defect class, and a second defect class results in C equaling "2" for feature vectors obtained from specimens having the second defect class. Each class value may correspond to a particular defect composition, a defect location relative to the substrate, a via, or a trench, an electrical short type defect, an electrical open type defect, etc. The class may also correspond to other characteristics of the specimen, besides a defect class, such as film thickness. In the above example, a class code equal to "1" may indicate a $SiO_2$ particle defect, while a class code equal to "2" may correspond to a copper particle defect.

If the class code values for a same class are not equal, the weight values are adjusted in operation 614 and operations 606 and 608 are repeated to obtain new class code values for the new adjusted weight values. If the class code values for the feature vectors having a same class have a same value, the weight values and the class code values and their associated known characteristics are stored for the pattern recognition process in operation 612. The procedure for setting up the pattern recognition process 504 then ends.

Figure 7:
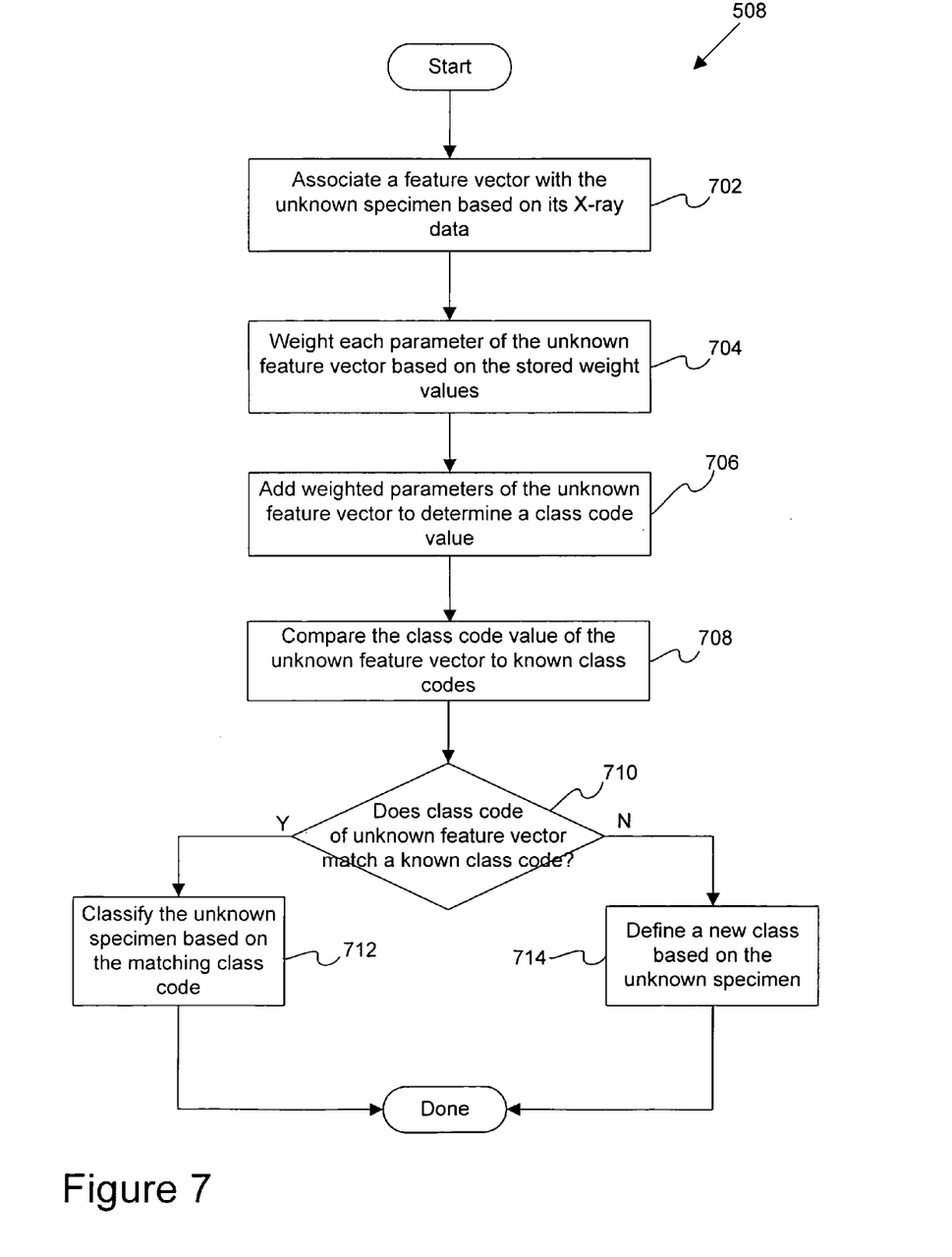
FIG. 7 is a flowchart illustrating the operation of FIG. 5 of using the pattern recognition process to identify or classify unknown specimens in accordance with one embodiment of the present invention.

FIG. 7 is a flowchart illustrating the operation 508 of FIG. 5 of using the pattern recognition process to identify or classify unknown specimens in accordance with one embodiment of the present invention. Initially, a feature vector is associated with the unknown specimen based on its X-ray data in operation 702. The feature vector preferably have the same parameters as the feature vectors used to set up the pattern recognition process of FIG. 6. Each parameter of the unknown feature vector and the stored weight values (determined and stored during the set up of the pattern recognition process of FIG. 6) are then input into the class code equation in operation 704. The class code value of the unknown feature vector is then compared to known class codes (determined and stored during the set up of the pattern recognition process of FIG. 6) in operation 708.

It is then determined whether the class code of the unknown feature vector matches a known class code in operation 710. If there is a match, the unknown specimen is then classified based on the matching class code and its associated known characteristic or defect class in operation 712. In the above example, if the class code value equals "2", it is determined that the specimen has the second type of defect, e.g., a copper particle defect. If there is no match found, a new class may then be defined based on the unknown specimen in operation 714. For instance, a new defect type may be manually classified by an operator and given a class code. The X-ray data from the new defect type may then be used to set up the weights for the class code equation so that it equals the new class code. As more defects of the same type are found, the weights of the class code equation can be adjusted based on the new X-ray data. After an unknown defect is classified, the pattern recognition process may then end or a new unknown specimen can then be analyzed.

Figure 8:
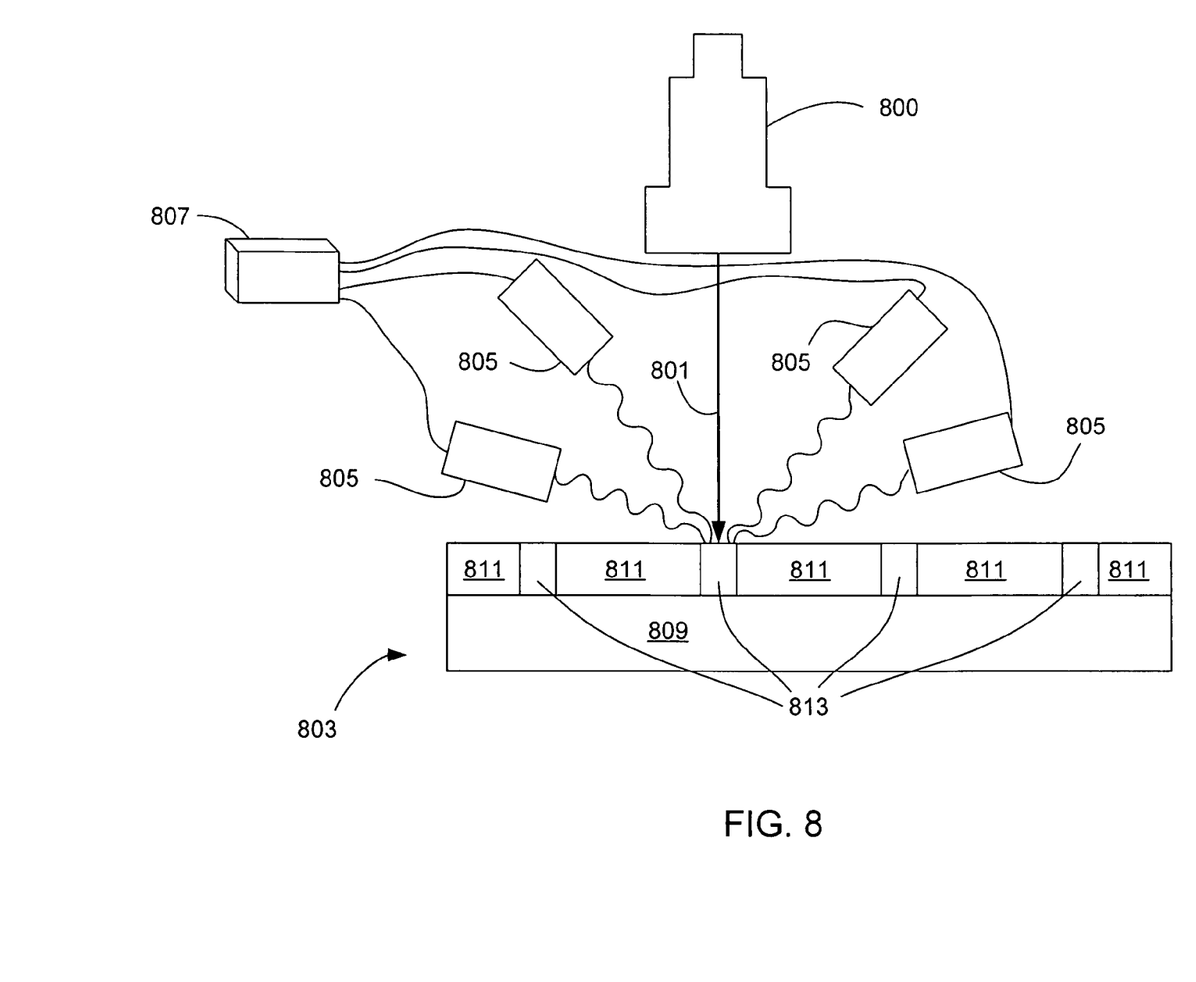
FIG. 8 is a diagrammatic representation of a system utilizing an electron beam induced X-ray microanalysis test system according to one embodiment of the present invention.

Any suitable electron beam induced X-ray microanalysis system may be utilized to practice and/or implement the techniques of the present invention. An eV300 automated e-Beam wafer inspection system available from KLA-Tencor Corporation of San Jose, Calif. may be used. FIG. 8 is a diagrammatic representation of a system utilizing an electron beam induced X-ray microanalysis test system according to one embodiment of the present invention. The system represented in FIG. 8 includes a beam generator 800, which directs an e-beam 801 at the specimen 803. The specimen 803 in the example depicted in FIG. 8 is a semiconductor wafer having a silicon substrate 809 upon which a silicon dioxide layer 811 is patterned with a plurality of trenches 813 filled with copper. The spot size of rastered beam may be any suitable size. Preferably, the spot size corresponds to approximately the area of the structure of interest. At least one X-ray detector is used to collect the X-rays emitted from the surface of the specimen. The system in FIG. 8 includes four X-ray detectors 805 positioned above the specimen.

Any suitable number and type of detector for measuring X-rays at specific energy levels may be utilized. One type of detector is an energy dispersive system (EDS), which collects photons in a wide spectrum of energies. EDS systems are capable of collecting a greater range of signals. As a result however, EDS detectors also collect photons having energies surrounding the characteristic photon energies. This causes EDS detectors to have lower signal to noise ratios. Another type of detector is a wavelength dispersive system (WDS) X-ray detector. Several suitable embodiments of WDS X-ray detectors are described further in co-pending U.S. patent application Ser. No. 09/695,726, filed 23 Oct. 2000, which application is incorporated herein by reference in its entirety.

In the system depicted in FIG. 8, each of the X-ray detectors is coupled with an analysis or processor unit 807. The analysis/processor unit 807 can be configured to analyze the data collected by the X-ray detectors 805 to generate X-ray ratio data of the elemental species in the specimen, such as the Cu L$\alpha$/Si K$\alpha$, Cu K$\alpha$/Si K$\alpha$ and Cu L$\alpha$/Cu K$\alpha$ described previously. The analysis/processor unit 807 may take the form of any suitable processing or computing system, such as a workstation, and include one or more processors and one or more memory devices.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of classifying specimens based on X-ray data obtained from such specimens, the method comprising:
   providing a plurality of differing X-ray data from a plurality of known specimens having differing known characteristics, wherein the differing known characteristics correspond to all of the specimens having the same known defect surrounded by differing known background structures;
   setting up a pattern recognition process to automatically classify the differing known characteristics of the known specimens into a same first class based on the differing X-ray data from the known specimens;
   providing X-ray data from an unknown specimen having an unknown characteristic of an unknown class; and
   utilizing the pattern recognition process to automatically classify the unknown characteristic of the unknown specimen as belonging to the first class based on the X-ray data from the unknown specimen.

2. A method as recited in claim 1, wherein providing the X-ray data from the known specimens comprises:
   directing a charged particle beam toward each known specimen; and
   detecting X-rays emitted from the each known specimen in response to the charged particle beam, wherein the detected X-rays form X-ray data having one or more intensity values at one or more energy levels.

3. A method as recited in claim 2, wherein providing the X-ray data from the unknown specimen comprises:
   directing a charged particle beam toward the unknown specimen; and
   detecting X-rays emitted from the unknown specimen in response to the charged particle beam, wherein the detected X-rays form X-ray data having one or more intensity values at one or more energy levels.

4. A method as recited in claim 1, wherein the unknown specimens and the known specimen are each a semiconductor device or test structure.

5. A method as recited in claim 1, wherein the first class is a known defect classes.

6. A method as recited in claim 5, wherein the known defect class includes a specified defect compositions.

7. A method as recited in claim 5, wherein the known defect class includes one or more characteristics selected from a group consisting of a particular defect composition, a defect location, an electrical type defect, and an open type defect.

8. A method as recited in claim 5, wherein the known defect class includes a particular film thickness.

9. A method as recited in claim 1, wherein setting up the pattern recognition process comprises:
   training a pattern recognition process to recognize particular types of X-ray data as belonging to the known class.

10. A method as recited in claim 9, wherein the pattern recognition process is selected from a group consisting of a neural net algorithm, a natural grouping algorithm, and a wavelet algorithm.

11. A method as recited in claim 1, wherein setting up the pattern recognition process comprises:
   associating a feature vector having a plurality of parameters with each known specimen based on the each known specimen's X-ray data;
   selecting a set of weight values for each variable in a class code equation;
   inputting the selected weight values and the parameters of each feature vector into the class code equation to determine a plurality of class codes for the known specimens;
   adjusting the weight values until the class codes for the known specimens class result in a same class code value; and
   storing the weight values and the class code value for the known specimens.

12. A method as recited in claim 11, wherein utilizing the pattern recognition process to automatically classify the unknown characteristic of the unknown specimen based on the X-ray data from the unknown specimen comprises:
   associating a feature vector having a plurality of parameters with the unknown specimen;
   inputting the stored weight values and the parameters of the feature vector of the unknown specimen into the class code equation to determine a class codes for the unknown specimen;
   comparing the class code for the unknown specimen to the stored class code for the known specimens; and
   when the class code for the unknown specimen matches a one of the stored class codes, classifying the unknown specimen based on the matching class code.

13. A method as recited in claim 12, wherein utilizing the pattern recognition process to automatically classify the unknown characteristic of the unknown specimen based on the X-ray data from the unknown specimen further comprises:
   when the class code for the unknown specimen does not match a one of the stored class codes, defining a new class code based on the X-ray data from the unknown specimen.

14. A method as recited in claim 12, wherein the parameters of each feature vector of the known specimens and the unknown specimen include intensity values for each X-ray peak and its associated energy level and/or one or more ratios of X-ray intensity values.

15. A method as recited in claim 14, wherein the parameters of each feature vector of the known specimens and the unknown specimen further include a defect size.

16. An apparatus for classifying specimens based on X-ray data obtained from such specimens, comprising:
   a beam generator operable to direct a charged particle beam towards a specimen;
   a detector positioned to detect X-rays from the specimen in response to the charged particle beam; and
   a processor operable to:
      provide a plurality of differing X-ray data from a plurality of known specimens having differing known characteristics, wherein the known characteristics correspond to all of the specimens having the same known defect surrounded by differing known background structures;
      set up a pattern recognition process to automatically classify the differing known characteristics of the known specimens into a same first class based on the differing X-ray data from the known specimens;
      provide X-ray data from an unknown specimen having an unknown characteristic of an unknown class; and
      utilize the pattern recognition process to automatically classify the unknown characteristic of the unknown specimen as belonging to the first class based on the X-ray data from the unknown specimen.

17. An apparatus as recited in claim 16, wherein providing the X-ray data from the known specimens comprises:
   directing a charged particle beam toward each known specimen; and
   detecting X-rays emitted from the each known specimen in response to the charged particle beam, wherein the detected X-rays form X-ray data having one or more intensity values at one or more energy levels.

18. An apparatus as recited in claim 17, wherein providing the X-ray data from the unknown specimen comprises:
   directing a charged particle beam toward the unknown specimen; and
   detecting X-rays emitted from the unknown specimen in response to the charged particle beam, wherein the detected X-rays form X-ray data having one or more intensity values at one or more energy levels.

19. An apparatus as recited in claim 16, wherein the unknown specimens and the known specimen are each a semiconductor device or test structure.

20. An apparatus as recited in claim 16, wherein the first class is a known defect classes.

21. An apparatus as recited in claim 20, wherein the known defect class includes defect compositions.

22. An apparatus as recited in claim 16, wherein setting up the pattern recognition process comprises:
   training a pattern recognition process to recognize particular types of X-ray data as belonging to the known class.

23. An apparatus as recited in claim 22, wherein the pattern recognition process is selected from a group consisting of a neural net algorithm, a natural grouping algorithm, and a wavelet algorithm.

24. An apparatus as recited in claim 16, wherein setting up the pattern recognition process comprises:
   associating a feature vector having a plurality of parameters with each known specimen based on the each known specimen's X-ray data;
   selecting a set of weight values for each variable in a class code equation;
   inputting the selected weight values and the parameters of each feature vector into the class code equation to determine a plurality of class codes for the known specimens;
   adjusting the weight values until the class codes for the known specimens class result in a same class code value; and
   storing the weight values and the class code value for the known specimens.

25. An apparatus as recited in claim 24, wherein utilizing the pattern recognition process to automatically classify the unknown characteristic of the unknown specimen based on the X-ray data from the unknown specimen comprises:
   associating a feature vector having a plurality of parameters with the unknown specimen;
   inputting the stored weight values and the parameters of the feature vector of the unknown specimen into the class code equation to determine a class codes for the unknown specimen;
   comparing the class code for the unknown specimen to the stored class codes for the known specimens; and
   when the class code for the unknown specimen matches a one of the stored class code, classifying the unknown specimen based on the matching class code.

26. An apparatus as recited in claim 25, wherein utilizing the pattern recognition process to automatically classify the unknown characteristic of the unknown specimen based on the X-ray data from the unknown specimen further comprises:
   when the class code for the unknown specimen does not match a one of the stored class codes, defining a new class code based on the X-ray data from the unknown specimen.

27. An apparatus as recited in claim 25, wherein the parameters of each feature vector of the known specimens and the unknown specimen include intensity values for each X-ray peak and its associated energy level and/or one or more ratios of X-ray intensity values.

* * * * *

UNITED STATES PATENT AND TRADEMARK OFFICE
CERTIFICATE OF CORRECTION

| | | |
|---|---|---|
| PATENT NO. | : 7,132,652 B1 | Page 1 of 1 |
| APPLICATION NO. | : 10/811319 | |
| DATED | : November 7, 2006 | |
| INVENTOR(S) | : Anne L. Testoni | |

It is certified that error appears in the above-identified patent and that said Letters Patent is hereby corrected as shown below:

In line 2 of claim 5 (column 10, line 9) change "classes" to --class--.

In line 2 of claim 20 (column 11, line 52) change "classes" to --class--.

Signed and Sealed this

Thirty-first Day of July, 2007

JON W. DUDAS
*Director of the United States Patent and Trademark Office*